US009012664B2

(12) United States Patent
Corbin et al.

(10) Patent No.: US 9,012,664 B2
(45) Date of Patent: *Apr. 21, 2015

(54) PROCESS FOR THE PRODUCTION OF FURFURAL

(71) Applicant: E I du Pont de Nemours and Company, Wilmington, DE (US)

(72) Inventors: David Richard Corbin, West Chester, PA (US); Paul Joseph Fagan, Wilmington, DE (US); Stuart B Fergusson, Kingston (CA); Keith W Hutchenson, Lincoln University, PA (US); Pranit S Metkar, Wilmington, DE (US); Ronnie Ozer, Arden, DE (US); Carmo Joseph Pereira, Silver Spring, MD (US); Bhuma Rajagopalan, Wilmington, DE (US); Sourav Kumar Sengupta, Wilmington, DE (US); Eric J. Till, Newtown Square, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 4 days.

This patent is subject to a terminal disclaimer.

(21) Appl. No.: 13/729,445

(22) Filed: Dec. 28, 2012

(65) Prior Publication Data

US 2013/0172583 A1 Jul. 4, 2013

Related U.S. Application Data

(60) Provisional application No. 61/580,717, filed on Dec. 28, 2011.

(51) Int. Cl.
*C07D 307/48* (2006.01)
*C07D 307/50* (2006.01)

(52) U.S. Cl.
CPC ............ *C07D 307/48* (2013.01); *C07D 307/50* (2013.01)

(58) Field of Classification Search
USPC ........................................................ 549/489
See application file for complete search history.

(56) References Cited

U.S. PATENT DOCUMENTS

| | | |
|---|---|---|
| 2,536,732 A | 1/1951 | Dunlop |
| 2,559,607 A | 7/1951 | Dunning |
| 2,750,394 A | 6/1956 | Peniston |
| 4,154,744 A | 5/1979 | Hamada |
| 4,366,322 A | 12/1982 | Raymond |
| 4,503,023 A | 3/1985 | Breck |
| 4,533,743 A | 8/1985 | Medeiros |
| 6,441,202 B1 | 8/2002 | Lightner |
| 6,743,928 B1 | 6/2004 | Hanna |
| 7,572,925 B2 | 8/2009 | Dumesic |
| 8,277,521 B2 | 10/2012 | Gruter |
| 8,314,260 B2 | 11/2012 | Gruter |
| 8,389,749 B2 | 3/2013 | Dumesic |
| 8,399,688 B2 | 3/2013 | Dumesic |
| 2003/0032819 A1 | 2/2003 | Lightner |
| 2007/0298477 A1 | 12/2007 | Kratochvil |
| 2008/0033187 A1 | 2/2008 | Zhao |
| 2008/0033188 A1 | 2/2008 | Dumesic |
| 2009/0124839 A1 | 5/2009 | Dumesic |
| 2009/0131690 A1 | 5/2009 | Gruter |
| 2009/0156841 A1 | 6/2009 | Sanborn |
| 2009/0306415 A1 | 12/2009 | Gruter |
| 2010/0048924 A1 | 2/2010 | Srinivas |
| 2010/0058650 A1 | 3/2010 | Gruter |
| 2010/0083565 A1* | 4/2010 | Gruter ............................ 44/350 |
| 2010/0212218 A1 | 8/2010 | Gruter |
| 2010/0218415 A1 | 9/2010 | Gruter |
| 2010/0218416 A1 | 9/2010 | Gruter |
| 2010/0299991 A1 | 12/2010 | Gruter |
| 2010/0317879 A1 | 12/2010 | Zhao |
| 2011/0071306 A1 | 3/2011 | Robinson |
| 2011/0144359 A1* | 6/2011 | Heide et al. ................... 549/489 |
| 2012/0108829 A1* | 5/2012 | de Jong et al. ................ 549/489 |
| 2012/0111714 A1 | 5/2012 | Court |
| 2012/0157697 A1 | 6/2012 | Burket |
| 2013/0017579 A1 | 1/2013 | Luterbacher |

FOREIGN PATENT DOCUMENTS

| | | |
|---|---|---|
| CN | 100999677 A | 7/2007 |
| CN | 101367782 A | 2/2009 |
| CN | 101486695 A | 7/2009 |
| EP | 2033958 A1 | 3/2009 |
| GB | 799603 A | 8/1958 |

(Continued)

OTHER PUBLICATIONS

Moreau, C., Selective preparation of furfural from xylose over microporous solid acid catalysts, 1998, Industrial Crops and Products 7, 95-99.*
Cheremisinoff, N.P., Liquid Filtration, 1998, Butterworth-Heinemann, Chapter 1, p. 14.*
Minton, P.E., Handbook of Filtration Technology, 1986, Noyes Publications, Chapter 2, p. 2.*
Cejka, J., Kirk-Othmer Encyclopedia of Chemical Technology,Zeolites and Other Micro- and Mesoporous Molecular Sieves, John Wiley and Sons, Online ISBN: 9780471238966; DOI: 10.1002/0471238961, p. 1-30.*
Bicker, M., Dehydration of fructose to 5-hydroxymethylfurfural in sub- and supercritical acetone, 2003, Green Chemistry, 5, 280-284.*

(Continued)

*Primary Examiner* — Noble Jarrell
*Assistant Examiner* — John Mauro

(57) ABSTRACT

Furfural is produced by contacting a feedstock solution containing $C_5$ sugar and/or $C_6$ sugar with a solid acid catalyst using reactive distillation. Both high yield and high conversion are obtained, without production of insoluble char in the reaction vessel. Degradation of furfural is minimized by its low residence time in contact with the solid acid catalyst. Higher catalyst lifetime can be achieved because the catalyst is continually washed with the refluxing aqueous solution and not sitting in high-boiling byproducts like humins, which are known to be deleterious to catalyst lifetime.

14 Claims, 1 Drawing Sheet

(56) References Cited

FOREIGN PATENT DOCUMENTS

| | | |
|---|---|---|
| GB | 838957 A | 6/1960 |
| JP | 02-108682 A | 4/1990 |
| JP | 10265468 A | 10/1998 |
| JP | 12065468 A | 10/1998 |
| JP | 2007196174 A | 8/2007 |
| WO | 0047569 A1 | 8/2000 |
| WO | 2011063500 A1 | 6/2011 |

OTHER PUBLICATIONS

Shanjiao, K., Preparation and Characterization of Zeolite Beta with Low SiO/Alz03 Ratio, 2007, Petroleum Science, 4(1), 70-74.*
Van Putten, R.-J., Hydroxymethylfurfural, A Versatile Platform Chemical Made from Renewable Resources, 2013, Chem. Rev. 113, 1499-1597.*
Cejka, J., Kirk-Othmer Encyclopedia of Chemical Technology,Zeolites and Other Micro- and Mesoporous Molecular Sieves, John Wiley and Sons, Apr. 16, 2010, Online ISBN: 9780471238966; DOI: 10.1002/0471238961, p. 1-30.*
Stichmair, J., Ullmann's Encyclopedia of Industrial Chemistry, 2010, Distillation, 1. Fundamentals, vol. 11, Published online Apr. 15, 2010, p. 425-454.*
Stichlmair, J., Distillation 1. Fundamentals, Ullmann's Encyclopedia of Industrial Chemistry, vol. 11, Published Online : Apr. 15, 2010, DOI: 10.1002/14356007.b03_04.pub2, p. 425-454.*
Baerlocher et al., Atlas of Zeolite Framework Types, 6th Revised Edition, Elsevier, Amsterdam, 2007. (Book—Not Included).
Karinen et al., Biorefining: Hetergeneously Catalyzed Reactions of Carbohydrates for the Production of Furfural and Hydroxymethylfurfural, Chem Sus Chem, vol. 4 (2011), pp. 1002-1016.
Chen, Hydrophobic Properties of Zeolites, Journal of Physical Chemistry, vol. 80, No. 1 (1976) pp. 60-64.
Dwyer, Zeolite Structure, Composition and Catalysis, Chemistry and Industry, vol. 2 (1984), pp. 258-269.
Szostak, Molecular Sieves Principles of Synthesis and Identification, Van Nostrand Reinhold, New York, 1989 (Book—Not Included).
International Search Report, PCT International Application No. PCT/US2012/071964, Mailed Apr. 26, 2013.
E. I. Fulmer et al., The Production of Furfural From Xylose Solutions by Means of Hydrochloric Acid-Sodium Chloride Systems, Department of Chemistry, Iowa, Journal of Physical Chemistry, vol. 40 (1936), pp. 133-141.
C. Liu et al., The Enhancement of Xylose Monomer and Xylotriose Degradation by Inorganic Salts in Aqueous Solutions At 180oC, Carbohydrate Research, vol. 341 (2006), pp. 2550-2556.
G. Marcotullio et al., Chloride Ions Enhance Furfural Formation From D-Xylose in Dilute Aqueous Acidic Solutions, Green Chemistry (2010), The Royal Society of Chemistry, pp. 1-8.

F. Tao et al., Efficient Process for the Conversion of Xylose to Furfural With Acidic Ionic Liquid, Can. J. Chem., vol. 89 (2011), pp. 83-87.
Blatter et al., The Preparation of Pure Zeolite Nay and Its Conversion to High-Silican Faujasite, J. Chem Ed., vol. 67 (1990), pp. 519-521.
Hutchings et al., Developments in the Production of Methyl Tert-Butyl Ether, Catalysis Today, vol. 15 (1992) pp. 23-49.
Baerlocher et al., Atlas of Zeolite Framework Types, $6^{th}$ Revised Edition, Elsevier, Amsterdam, 2007 (Book—Not Included)
Karinen et al., Biorefining: Heterogeneously Catalyzed Reactions of Carbohydrates for the Production of Furfural and Hydroxymethylfurfural, Chem Sus Chem, vol. 4 (2011) pp. 1002-1016.
Chen, Hydrophobic Properties of Zeolites, Journal of Physical Chemistry, vol. 80, No. 1 (1976) pp. 60-64.
Dwyer, Zeolite Structure, Composition and Catalysis, Chemistry and Industry, vol. 2 (1984) pp. 258-269.
Szostak, Molecular Seives Principles of Synthesis and Identification, Van Nostr and Reinhold, New York, 1989 (Book—Not Included).
Gairola et al., Hydrothermal Pentose to Furfural Conversion and Simultaneous Extraction With SC-CO2, Kinectics and Application to Biomass Hydrolysates, Bioresource Technology, vol. 123 (2012), pp. 592-598.
Kawamoto et al., Catalytic Pyrolysis of Cellulose in Sulfolane With Some Acidic Catalysts, J Wood Sci, vol. 53 (2007), pp. 127-133.
Suzuki et al., Dehydration of Xylose Over Sulfated Tin Oxide Catalyst: Influences of the Preparation Conditions on the Structural Properties and Catalytic Performance, Applied Catalysis A: General, vol. 408 (2011), pp. 117-124.
Starr et al., High Sulfidity Pulping in Aqueous Sulfolane,Tappi Alkaline Pulping Conference Preprints (1975), pp. 195-198.
Clermont, Delignification of Aspen Wood With Aqueous Sulfolane Solutions, Tappi, vol. 53, No. 12 (1970), pp. 2243-2245.
Chheda et al., Production of 5-Hydroxymethylfufual and furfural by dehydration of biomass-derived mono- and polysaccharides, Green Chemistry, 2007, 342-350, 9, The Royal Society of Chemistry.
Mamman et al., Furfural: Hemicellulose/xylose-derived biochemical, Biofuels, Bioproducts & Biorefining, 2008, 438-453, Wiley Interscience.
Vazquez et al., Hydrolysis of Sorghum Straw using Phosphoric Acid: Evaluation of Furfural Production, Bioresource Technology, 2007, 3053-3060, 98, Elsevier.
Amiri et al., Production of furans from rice straw by single-phase and biphasic systems, Carbohydrate Research, 2010, 2133-2138, vol. 345.
Weingarten et al., Kinetics of furfural production by dehydration of xylose in a biphasic reactor with microwave heating, Green Chemistry, The Royal Society of Chemistry, 2010, 1423-1429, vol. 12.
Zhao et al., Metal Chlorides in Ionic Liquid Solvents Convert Sugars to 5-Hydroxymethylfurfural, Science, 2007, 1597-1600, vol. 316.
Dias et al., Dehydration of xylose into furfural over micro-mesoporous sulfonic acid catalysts, Journal of Catalysis, 2005, 414-423, vol. 229.

* cited by examiner

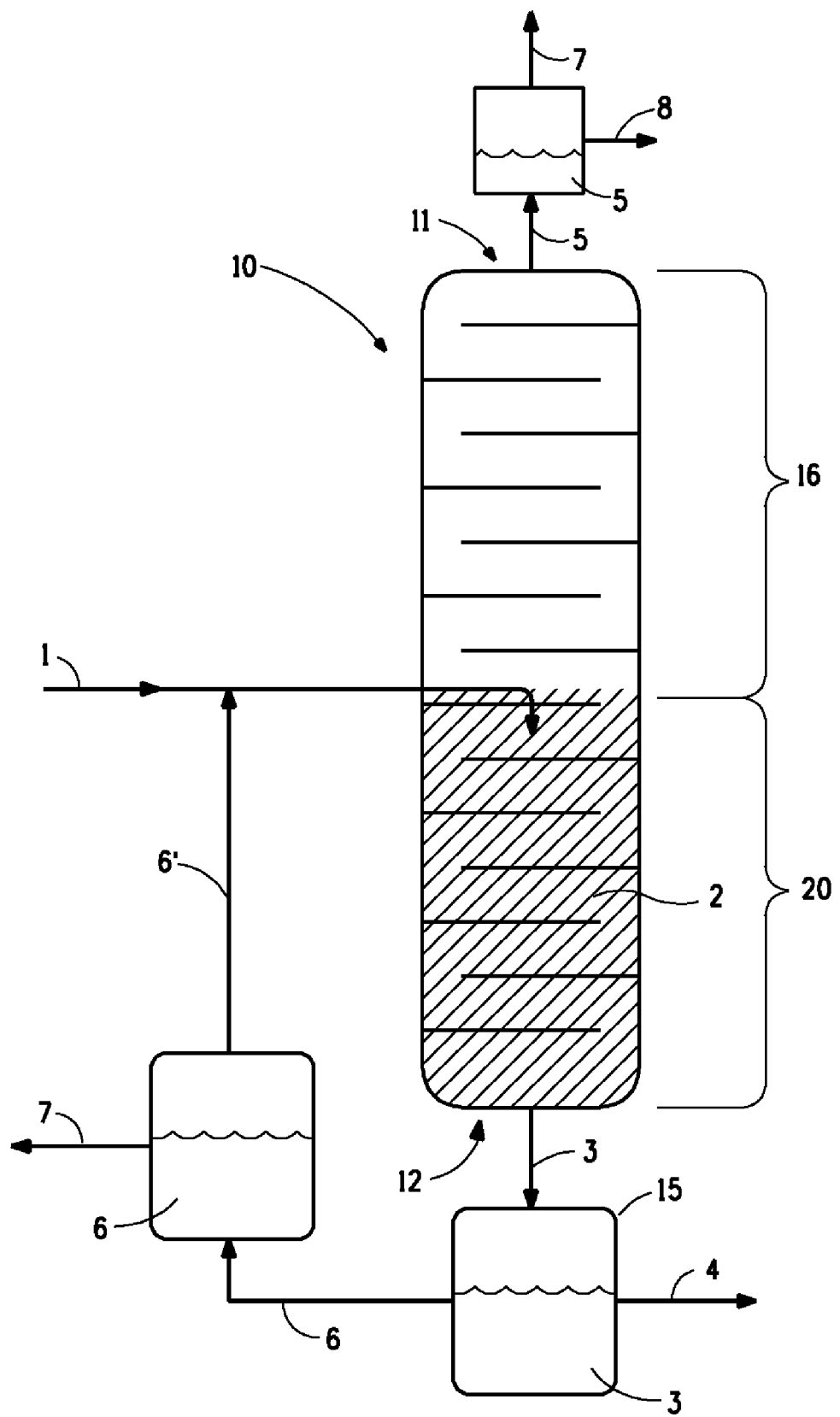

PROCESS FOR THE PRODUCTION OF FURFURAL

This application claims the benefit under 35 U.S.C. §119 (e) of U.S. Provisional Application No. 61/580,717, filed Dec. 28, 2011, which is herein incorporated by reference.

FIELD OF THE INVENTION

A method for the production of furfural and related compounds from sugar streams is provided.

BACKGROUND OF THE INVENTION

Furfural and related compounds, such as hydroxymethylfurfural (HMF), are useful precursors and starting materials for industrial chemicals for use as pharmaceuticals, herbicides, stabilizers, and polymers. The current furfural manufacturing process utilizes biomass such as corn cob and sugar cane bagasse as a raw material feed stock for obtaining xylose or hemicellulose.

The hemicellulose is hydrolyzed under acidic conditions to its monomer sugars, such as glucose, fructose, xylose, mannose, galactose, rhamnose, and arabinose. Xylose, which is a pentose (i.e., a "$C_5$ sugar") is the sugar present in the largest amount. In a similar aqueous acidic environment, the $C_5$ sugars are subsequently dehydrated and cyclized to furfural.

A major difficulty with known methods for dehydration of sugars is the formation of undesirable resinous material that not only leads to yield loss but also leads to fouling of exposed reactor surface and negatively impacts heat transfer characteristics. Further, the use of solid acid catalyst could also lead to coking issues.

A review by R. Karinen et al. (*ChemSusChem* 4 (2011), pp. 1002-1016) includes several commonly used methods of producing furfural generally as described above. All of those methods involve use of a soluble inorganic acid catalyst, such as sulfuric, phosphoric, or hydrochloric acid. These acids are difficult to separate from the reaction medium or product stream. Low yields can result from formation of undesirable byproducts. Further, their use can require increased capital costs because of associated corrosion and environmental emission issues.

There remains a need for a process to produce furfural and related compounds from sugars at both high yield and high conversion.

SUMMARY OF THE INVENTION

In an aspect of the invention, there is a process comprising:
(a) providing a reactive distillation column comprising a top, a bottom, a reaction zone in between the top and the bottom, and a solid acid catalyst disposed in the reaction zone;
(b) bringing a feedstock solution into contact with the solid acid catalyst for a residence time sufficient to produce a mixture of water and furfural, wherein the feedstock solution comprises $C_5$ sugar, $C_6$ sugar or a mixture thereof, and the reaction zone is at a temperature in the range of 90-250° C. and a pressure in the range of 0.1-3.87 MPa;
(c) removing the mixture of water and furfural from the top of the reactive distillation column; and
(d) collecting water, unreacted sugars and nonvolatile byproducts from the bottom of the reactive distillation column.

In an aspect, the process further comprises feeding a water-miscible organic solvent to the reaction zone.

In another aspect, the feedstock solution further comprises a water-miscible organic solvent.

In another aspect, there is a process comprising the steps of:
(a) providing a reactor comprising a reactive distillation column comprising an upper, rectifying section; a lower, stripping section; and a reboiler, wherein the stripping section or the reboiler is a reaction zone containing a solid acid catalyst;
(b) continuously feeding a solution comprising $C_5$ sugar, $C_6$ sugar or a mixture thereof to the column at a location between the rectifying section and the stripping section, allowing the solution to flow into the reaction zone into contact with the solid acid catalyst, thereby forming a reaction mixture, wherein
  (i) the temperature of the reaction mixture is between about 90° C. and about 250° C.
  (ii) the reaction mixture is held at a pressure between about atmospheric pressure and about $3.87 \times 10^6$ Pa, and
  (iii) the sugar solution and catalyst are in contact for a time sufficient to produce water and furfural;
(c) drawing off a mixture of furfural and water at the top of the column;
(d) collecting water, unreacted sugars, and nonvolatile byproducts in the reboiler;
(e) removing nonvolatile byproducts from the reboiler; and
(f) removing the water and unreacted sugars from the reboiler for further use or disposal.

BRIEF DESCRIPTION OF THE DRAWINGS

Various features and/or embodiments of this invention are illustrated in drawings as described below. These features and/or embodiments are representative only, and the selection of these features and/or embodiments for inclusion in the drawings should not be interpreted as an indication that subject matter not included in the drawings is not suitable for practicing the invention, or that subject matter not included in the drawings is excluded from the scope of the appended claims and equivalents thereof.

FIG. 1 is a schematic illustration of an exemplary reactor configuration used in the production of furfural in accordance with various embodiments of the present invention.

DETAILED DESCRIPTION

Definitions

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; some examples are xylose, arabinose, lyxose and ribose. A hexose is a monosaccharide having six carbon atoms; some examples are glucose and fructose. Disaccharide molecules (e.g., sucrose, lactose, fructose, and maltose) consist of two covalently linked monosaccharide units. As used herein, "oligosaccharide" molecules consist of about 3 to about 20 covalently linked monosaccharide units.

As used herein, the term "$C_n$ sugar" includes monosaccharides having n carbon atoms; disaccharides comprising monosaccharide units having n carbon atoms; and oligosaccharides comprising monosaccharide units having n carbon atoms. Thus, "$C_5$ sugar" includes pentoses, disaccharides comprising pentose units, and oligosaccharides comprising pentose units.

As used herein, the term "hemicellulose" refers to a polymer comprising $C_5$ and $C_6$ monosaccharide units. Hemicellulose consists of short, highly branched chains of sugars. In contrast to cellulose, which is a polymer of only glucose, a hemicellulose is a polymer of five different sugars. It contains five-carbon sugars (usually D-xylose and L-arabinose) and six-carbon sugars (D-galactose, D-glucose, and D-mannose, fructose). Hemicellulose can also contain uronic acid, sugars in which the terminal carbon's hydroxyl group has been oxidized to a carboxylic acid, such as, D-glucuronic acid, 4-O-methyl-D-glucuronic acid, and D-galacturonic acid. The sugars are partially acetylated. Typically the acetyl content is 2 to 3% by weight of the total weight of hemicellulose. Xylose is typically the sugar monomer present in hemicellulose in the largest amount.

As used herein, the term "solid acid catalyst" refers to any solid material containing Brönsted and/or Lewis acid sites, and which is substantially undissolved by the reaction medium under ambient conditions.

As used herein, the term "nonvolatile byproduct" denotes a reaction byproduct that either has a boiling point at one atmospheric pressure greater than the boiling point of the distilled product(s), or is a nonvolatile solid.

As used herein, the term "heteropolyacid" denotes an oxygen-containing acid with P, As, Si, or B as a central atom which is connected via oxygen bridges to W, Mo or V. Some examples are phosphotungstic acid, molybdophosphoric acid.

As used herein, the term "high boiling" denotes a solvent having a boiling point above about 100° C. at one atmosphere.

As used herein the term "water-miscible organic solvent" refers to an organic solvent that can form a monophasic solution with water at the temperature at which the reaction is carried out.

As used herein the term "humin(s)" refers to dark, amorphous byproduct(s) resulting from acid induced sugar and furfural degradation.

As used herein, the term "selectivity" refers to the moles of furfural produced, divided by the moles of xylose transformed to products over a particular time period.

In an embodiment, there is a process for the production of furfural comprising providing a reactive distillation column comprising a top, a bottom, a reaction zone in between the top and the bottom, and a solid acid catalyst disposed in the reaction zone. FIG. 1 shows a schematic illustration of an exemplary reactor configuration comprising a reactive distillation column 10 comprising a top 11, a bottom 12, a reaction zone 20 in between the top 11 and the bottom 12, and a solid acid catalyst 2 disposed in the reaction zone 20.

The solid acid catalyst is a solid acid having the thermal stability required to survive reaction conditions. The solid acid catalyst may be supported on at least one catalyst support. Examples of suitable solid acids include without limitation the following categories: 1) heterogeneous heteropolyacids (HPAs) and their salts, 2) natural or synthetic clay minerals, such as those containing alumina and/or silica (including zeolites), 3) cation exchange resins, 4) metal oxides, 5) mixed metal oxides, 6) metal salts such as metal sulfides, metal sulfates, metal sulfonates, metal nitrates, metal phosphates, metal phosphonates, metal molybdates, metal tungstates, metal borates, and 7) combinations of any members of any of these categories. The metal components of categories 4 to 6 may be selected from elements from Groups 1 through 12 of the Periodic Table of the Elements, as well as aluminum, chromium, tin, titanium, and zirconium. Examples include, without limitation, sulfated zirconia and sulfated titania.

Suitable HPAs include compounds of the general formula $X_aM_bO_c^{q-}$, where X is a heteroatom such as phosphorus, silicon, boron, aluminum, germanium, titanium, zirconium, cerium, cobalt or chromium, M is at least one transition metal such as tungsten, molybdenum, niobium, vanadium, or tantalum, and q, a, b, and c are individually selected whole numbers or fractions thereof. Nonlimiting examples of salts of HPAs are lithium, sodium, potassium, cesium, magnesium, barium, copper, gold and gallium, and onium salts such as ammonia. Methods for preparing HPAs are well known in the art and are described, for example, in G. J. Hutchings, C. P. Nicolaides and M. S. Scurrel, Catal Today (1994) p 23; selected HPAs are also available commercially, for example, through Sigma-Aldrich Corp. (St. Louis, Mo.). Examples of HPAs suitable for the disclosed process include, but are not limited to, tungstosilicic acid ($H_4[SiW_{12}O_{40}].xH_2O$), tungstophosphoric acid ($H_3[PW_{12}O_{40}].xH_2O$), molybdophosphoric acid ($H_3[PMo_{12}O_{40}].xH_2O$), molybdosilicic acid ($H_4[SiMo_{12}O_{40}].xH_2O$), vanadotungstosilicic acid ($H_{4+n}[SiV_nW_{12-n}O_{40}].xH_2O$), vanadotungstophosphoric acid ($H_{3+n}[PV_nW_{12-n}O_{40}].xH_2O$), vanadomolybdophosphoric acid ($H_{3+n}[PV_nMo_{12-n}O_{40}].xH_2O$), vanadomolybdosilicic acid ($H_{4+n}[SiV_nMo_{12-n}O_{40}].xH_2O$), molybdotungstosilicic acid ($H_4[SiMo_nW_{12-n}O_{40}].xH_2O$), molybdotungstophosphoric acid ($H_3[PMo_nW_{12-n}O_{40}].xH_2O$), wherein n in the formulas is an integer from 1 to 11 and x is an integer of 1 or more.

Natural clay minerals are well known in the art and include, without limitation, kaolinite, bentonite, attapulgite, montmorillonite and zeolites.

In an embodiment, the solid acid catalyst is a cation exchange resin that is a sulfonic-acid-functionalized polymer. Suitable cation exchange resins include, but are not limited to the following: styrene-divinylbenzene copolymer-based strong cation exchange resins such as Amberlyst™ and Dowex® available from Dow Chemicals (Midland, Mich.) (for example, Dowex® Monosphere M-31, Amberlyst™ 15, Amberlite™ 120); CG resins available from Resintech, Inc. (West Berlin, N.J.); Lewatit resins such as MonoPlus™ S 100H available from Sybron Chemicals Inc. (Birmingham, N.J.); fluorinated sulfonic acid polymers (these acids are partially or totally fluorinated hydrocarbon polymers containing pendant sulfonic acid groups, which may be partially or totally converted to the salt form) such as Nalion® perfluorinated sulfonic acid polymer, Nafion® Super Acid Catalyst (a bead-form strongly acidic resin which is a copolymer of tetrafluoroethylene and perfluoro-3,6-dioxa-4-methyl-7-octene sulfonyl fluoride, converted to either the proton ($H^+$), or the metal salt form) available from DuPont Company (Wilmington, Del.).

In an embodiment, the solid acid catalyst is a supported acid catalyst. The support for the solid acid catalyst can be any solid substance that is inert under the reaction conditions including, but not limited to, oxides such as silica, alumina, titania, sulfated titania, and compounds thereof and combinations thereof; barium sulfate; calcium carbonate; zirconia; carbons, particularly acid washed carbon; and combinations thereof. Acid washed carbon is a carbon that has been washed with an acid, such as nitric acid, sulfuric acid or acetic acid, to remove impurities. The support can be in the form of powder, granules, pellets, or the like. The supported acid catalyst can be prepared by depositing the acid catalyst on the support by any number of methods well known to those skilled in the art of catalysis, such as spraying, soaking or physical mixing, followed by drying, calcination, and if necessary, activation through methods such as reduction or oxidation. The loading of the at least one acid catalyst on the at least one support is in the range of 0.1-20 weight based on the combined weights of the at least one acid catalyst and the at least one support. Certain acid catalysts perform better at low loadings such as 0.1-5%, whereas other acid catalysts are more likely to be useful at higher loadings such as 10-20%. In an embodiment, the acid catalyst is an unsupported catalyst having 100% acid catalyst with no support such as, pure zeolites and acidic ion exchange resins.

Examples of supported solid acid catalysts include, but are not limited to, phosphoric acid on silica, Nafion® perfluorinated sulfonic acid polymer on silica, HPAs on silica, sulfated zirconia, and sulfated titania. In the case of Nafion® on silica, a loading of 12.5% is typical of commercial examples.

In another embodiment, the solid acid catalyst comprises Amberlyst™ 70.

In one embodiment, the solid acid catalyst comprises a Nafion® supported on silica ($SiO_2$).

In one embodiment, the solid acid catalyst comprises natural or synthetic clay minerals, such as those containing alumina and/or silica (including zeolites).

Zeolites suitable for use herein can be generally represented by the following formula $M_{2/n}O.Al_2O_3.xSiO_2.yH_2O$ wherein M is a cation of valence n, x is greater than or equal to about 2, and y is a number determined by the porosity and the hydration state of the zeolite, generally from about 2 to about 8. In naturally occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

The zeolite framework structure has corner-linked tetrahedra with Al to or Si atoms at centers of the tetrahedra and oxygen atoms at the corners. Such tetrahedra are combined in a well-defined repeating structure comprising various combinations of 4-, 6-, 8-, 10-, and 12-membered rings. The resulting framework structure is a pore network of regular channels and cages that is useful for separation. Pore dimensions are determined by the geometry of the aluminosilicate tetrahedra forming the zeolite channels or cages, with nominal openings of about 0.26 nm for 6-member rings, about 0.40 nm for 8-member rings, about 0.55 nm for 10-member rings, and about 0.74 nm for 12-member rings (these numbers assume the ionic radii for oxygen). Zeolites with the largest pores, being 8-member rings, 10-member rings, and 12-member rings, are frequently considered small, medium and large pore zeolites, respectively.

In a zeolite, the term "silicon to aluminum ratio" or, equivalently, "Si/Al ratio" means the ratio of silicon atoms to aluminum atoms. Pore dimensions are critical to the performance of these materials in catalytic and separation applications, since this characteristic determines whether molecules of certain size can enter and exit the zeolite framework.

In practice, it has been observed that very slight decreases in ring dimensions can effectively hinder or block movement of particular molecular species through the zeolite structure. The effective pore dimensions that control access to the interior of the zeolites are determined not only by the geometric dimensions of the tetrahedra forming the pore opening, but also by the presence or absence of ions in or near the pore. For example, in the case of zeolite type A, access can be restricted by monovalent ions, such as $Na^+$ or $K^+$, which are situated in or near 8-member ring openings as well as 6-member ring openings. Access can be enhanced by divalent ions, such as $Ca^{2+}$, which are situated only in or near 6-member ring openings. Thus, the potassium and sodium salts of zeolite A exhibit effective pore openings of about 0.3 nm and about 0.4 nm respectively, whereas the calcium salt of zeolite A has an effective pore opening of about 0.5 nm.

The presence or absence of ions in or near the pores, channels and/or cages can also significantly modify the accessible pore volume of the zeolite for sorbing materials. Representative examples of zeolites are (i) small pore zeolites such as NaA (LTA), CaA (LTA), Erionite (ERI), Rho (RHO), ZK-5 (KFI) and chabazite (CHA); (ii) medium pore zeolites such as ZSM-5 (MFI), ZSM-11 (MEL), ZSM-22 (TON), and ZSM-48 (*MRE); and (iii) large pore zeolites such as zeolite beta (BEA), faujasite (FAU), mordenite (MOR), zeolite L (LTL), NaX (FAU), NaY (FAU), DA-Y (FAU) and CaY (FAU). The letters in parentheses give the framework structure type of the zeolite. Definitions of zeolite framework types may be found in the following references: http://www.iza-structure.org/, and Baerlocher, McCusker, Olson["Atlas of Zeolite Framework Types, $6^{th}$ revised edition, Elsevier, Amsterdam].

Zeolites suitable for use herein include medium or large pore, acidic, hydrophobic zeolites, including without limitation ZSM-5, faujasites, beta, mordenite zeolites or mixtures thereof, having a high silicon to aluminum ratio, such as in the range of 5:1 to 400:1 or 5:1 to 200:1. Medium pore zeolites have a framework structure consisting of 10-membered rings with a pore size of about 0.5-0.6 nm. Large pore zeolites have a framework structure consisting of 12-membered rings with a pore size of about 0.65 to about 0.75 nm. Hydrophobic zeolites generally have Si/Al ratios greater than or equal to about 5, and the hydrophobicity generally increases with increasing Si/Al ratios. Other suitable zeolites include without limitation acidic large pore zeolites such as H—Y with Si/Al in the range of about 2.25 to 5.

Zeolites with a high Si/Al ratio can be prepared synthetically, or by modification of high alumina containing zeolites using methods known in the art. These methods include without limitation treatment with $SiCl_4$ or $(NH_4)_2SiF_6$ to replace Al with Si, as well as treatment with steam followed by acid. A $SiCl_4$ treatment is described by Blatter [J. Chem. Ed. 67 (1990) 519]. A $(NH_4)_2SiF_6$ treatment is described in U.S. Pat. No. 4,503,023. These treatments are generally very effective at increasing the Si/Al ratio for zeolites such as zeolites Y and mordenite.

The presence of aluminum atoms in the frameworks results in hydrophilic sites. On removal of these framework aluminum atoms, water adsorption is seen to decrease and the material becomes more hydrophobic and generally more organophilic. Hydrophobicity in zeolites is further discussed by Chen [J. Phys. Chem. 80 (1976) 60]. Generally, high Si/Al containing zeolites exhibit higher thermal and acid stability. Acid forms of zeolites can be prepared by a variety of techniques including ammonium exchange followed by calcination or by direct exchange of alkali ions for protons using mineral acids or ion exchangers. Acid sites in zeolites are further discussed in Dwyer, "Zeolite, Structure, Composition and Catalysis" in Chemistry and Industry, Apr. 2, 1984.

Certain types of molecular sieves, of which zeolites are a sub-type, may also be used as the catalytic material in the processes hereof. While zeolites are aluminosilicates, molecular sieves contain other elements in place of aluminum and silicon, but have analogous structures. Large pore, hydrophobic molecular sieves that have similar properties to the preferred zeolites described above are suitable for use herein. Examples of such molecular sieves include without limitation Ti-Beta, B-Beta, and Ga-Beta silicates. Molecular sieves are further discussed in Szostak, *Molecular Sieves Principles of Synthesis and Identification*, (Van Nostrand Reinhold, NY, 1989).

Referring back to the process for the production of furfural, the process also comprises, as shown in FIG. 1 bringing a feedstock solution 1 into contact with the solid acid catalyst 2 for a residence time sufficient to produce a mixture 5 of water 7 and furfural 8 in the reaction zone 20. In an embodiment, the feedstock solution 1 comprises $C_5$ sugar, $C_6$ sugar or a mixture thereof dissolved in water, or a high boiling water-miscible organic solvent, or a mixture thereof. In another embodiment, the reaction zone is at a temperature in the range of 90-250° C. and a pressure in the range of 0.1-3.87 MPa.

The feedstock solution comprises at least one $C_5$ sugar, at least one $C_6$ sugar, or a mixture of at least one $C_5$ sugar and at least one $C_6$ sugar. Examples of suitable $C_5$ sugars, pentoses include without limitation xylose, arabinose, lyxose and ribose. Examples of suitable $C_6$ sugars, hexoses include without limitation glucose, fructose, mannose, and galactose.

In one embodiment, the feedstock solution comprises xylose. In another embodiment, the feedstock solution comprises glucose. In another embodiment, the feedstock solution comprises xylose and glucose.

The total sugar ($C_5$ sugar, $C_6$ sugar, or a mixture thereof) is present in the feedstock solution in the range of 1-99 weight % or 0.1-50 weight % or 5-35 weight % or 5-10 weight %, based on the total weight of the feedstock solution. In an embodiment, the feedstock solution 1 is an aqueous feedstock solution.

As shown in the FIG. 1, the feedstock solution 1 is added to the distillation column 10 at a location between the rectifying section 16 and the reaction zone 20 at a rate that provides sufficient residence time in the reaction zone 20 (which is also the stripping section) for complete or nearly complete conversion of sugars to furfural. The required residence time is a function of temperature and sugar concentration and is readily determined by one of skill in the art. In an embodiment, the residence time in the reaction zone is in the range of 1-500 min or 1-250 min or 5-120 min. The feedstock solution 1 flows down through the reaction zone 20 and is converted to a mixture 5 of furfural 8 and water 7 which is then partially vaporized and refluxes as part of the distillation column 10.

The temperature of the feedstock solution in the reaction zone 20 is in the range of 90-250° C. or 140-220° C. or 155-200° C.

The reaction is carried at a pressure between about atmospheric pressure and 3.87 MPa or 0.1-3.4 MPa or 0.1-2.0 MPa. In an embodiment, the feedstock solution is an aqueous feedstock solution and the reaction is carried at a pressure in the range of 0.5-1.6 MPa. In another embodiment, the feedstock solution comprises a high boiling water-miscible organic solvent, and the reaction is carried at about atmospheric pressure.

The process for the production of furfural further comprises removing the mixture 5 of water and furfural from the top 11 of the reactive distillation column 10 and collecting water and/or solvent unreacted sugars and nonvolatile byproducts into the reboiler 3 from the bottom of the reactive distillation column 10, as shown in FIG. 1.

As the reaction proceeds, a mixture 5 of vapors comprising one or more of furfural, water, acetic acid, acetone, and formic acid are removed from the reaction mixture via reflux through a multistage distillation column 10, condensed, and collected as a solution 5 of furfural and water. The use of staging in the distillation process allows more efficient stripping of furfural away from the acid catalyst solution. This increases furfural yield by driving the reaction toward completion and by minimizing formation of byproducts.

The sugar in the feedstock solution undergoes chemical transformation to furfural, which, along with water (from the aqueous feedstock and water produced by the reaction), is then drawn at the top 11 of the distillation column 10. This minimizes the residence time of furfural in the acidic environment of the reaction zone 20 and thereby minimizes its degradation. The furfural 8 is separated from the water and purified by any convenient methods known in the art, and the product furfural is removed. The water is either recycled to the source of the feedstock sugar solution or is released from the process.

Reaction byproducts 3, including, but not limited to, water, unreacted sugars, and non-volatile byproducts such as humins are collected in the reboiler 15 beneath the distillation column 10, as shown in FIG. 1. The nonvolatile byproducts 4 are removed from the reboiler 15 (e.g., by filtration). The solution 6 of water and unreacted sugars can be disposed of, or at least a portion can be concentrated by evaporation and fed as a stream 6' to be used as feedstock solution 1, as shown in FIG. 1.

In one embodiment, with reference to FIG. 1, the feedstock solution 1 is fed into the distillation column 10 at a location between the rectifying section 16 of the distillation column 10 and the reaction zone 20, above the solid catalyst 2. The catalyst 2 is included in the bottom, stripping section, which is the reaction zone 20. A mixture 5 of furfural and water (as steam) are drawn off at the top 11 of the column 5. Reaction byproducts 3 such as, water and/or solvent, unreacted sugars, and nonvolatile byproducts (e.g., humins and other higher boiling byproducts) are collected in the reboiler 15. The nonvolatile materials 4 are removed from the reboiler 15. The remaining solution 6 is concentrated by evaporation, with evaporated water vapor removed for disposal or reuse. The concentrated stream 6' is then fed back as the feedstock solution 1.

In an embodiment, the process comprises feeding a high boiling water-miscible organic solvent to the reaction zone 20, which would dissolve water-insoluble, nonvolatile byproducts such as humins. In one embodiment, the high boiling water-miscible organic solvent is added to the feedstock solution before feeding to the reaction zone 20. The nonvolatile byproducts can be removed diluting the remaining contents of the reboiler in a mixing chamber with water or aqueous feedstock solution, thereby precipitating water-insoluble byproducts; and removing the precipitated water-insoluble byproducts, e.g., by filtration or centrifugation and feeding the precipitate-free solution remaining back to the reaction zone 20.

The water-miscible organic solvent has a boiling point higher than about 100° C. at atmospheric pressure. Examples of suitable solvents include without limitation: sulfolane, polyethylene glycol, isosorbide dimethyl ether, isosorbide, propylene carbonate, poly(ethylene glycol) dimethyl ether, adipic acid, diethylene glycol, 1,3-propanediol, glycerol, gamma-butyrolactone, and gamma-valerolactone.

In one embodiment, the water-miscible organic solvent is sulfolane.

In one embodiment of the invention, the solvent is PEG 4600, PEG 10000, PEG 1000, polyethylene glycol, gamma-valerolactone, gamma-butyrolactone, isosorbide dimethyl ether, propylene carbonate, adipic acid, poly(ethylene glycol) dimethyl ether, isosorbide, Cerenol™ 270 (poly(1,3-propanediol), Cerenol™ 1000 ((poly(1,3-propanediol)), or diethylene glycol.

In one embodiment of the invention disclosed herein, a process is provided comprising the steps of:

(a) providing reactor comprising a reactive distillation column comprising an upper, rectifying section; a lower, stripping section; and a reboiler, wherein the stripping section or the reboiler is a reaction zone containing a solid acid catalyst, (b) continuously feeding an solution comprising $C_5$ sugar, $C_6$ sugar or a mixture thereof to the column at a location between the rectifying section and the stripping section, allowing the solution to flow into the reaction zone into contact with the solid acid catalyst, thereby forming a reaction mixture, wherein (i) the temperature of the reaction mixture is between about 90° C. and about 250° C.

(ii) the reaction mixture is held at a pressure between about atmospheric pressure and about $3.87 \times 10^6$ Pa, and (iii) the sugar solution and catalyst are in contact for a time sufficient to produce water and furfural;

(c) drawing off a mixture of furfural and water at the top of the column;

(d) collecting water, unreacted sugars, and nonvolatile byproducts in the reboiler;

(e) removing nonvolatile byproducts from the reboiler; and (f) removing the water and unreacted sugars from the reboiler for further use or disposal.

The combination of high yield and high conversion is desirable for a most efficient and economical process. In the event that a higher selectivity can be obtained at lower conversion, it may be desirable to run at lower conversion, for example 50-80%, and recycle unreacted sugars back to the reaction zone. The process described above produces furfural from solutions of C5 and/or C6 sugars at both high yield and medium to high conversion, without production of insoluble char in the reaction vessel. In an embodiment, the furfural yield is in the range of 40-95% or 60-95% or 65-85%. In another embodiment, the conversion of sugar to furfural is in the range of 10-100% or 25-100% or 50-100%. In an embodiment, the furfural selectivity is in the range of 40-95% or 60-95% or 65-85%

Degradation of furfural is minimized by its low residence time in contact with the solid acid catalyst. Higher catalyst lifetime can be achieved because the catalyst is continually washed with the refluxing solution and not in contact for long periods of time with high-boiling byproducts like humins, which are known to be deleterious to catalyst lifetime. Solid acid catalysts have the advantage of not inducing corrosion in the reaction vessels and other process equipment as compared to liquid acid catalysts.

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "invention" or "present invention" is a non-limiting term and is not intended to refer to any single variation of the particular invention but encompasses all possible variations described in the specification and recited in the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

EXAMPLES

The methods described herein are illustrated in the following examples. From the above discussion and these examples, one skilled in the art can ascertain the essential characteristics of this invention, and without departing from the spirit and scope thereof, can make various changes and modifications of the invention to adapt it to various uses and conditions.

Abbreviations

The meaning of abbreviations is as follows: "cm" means centimeter(s), "g" means gram(s), "h" means hour(s), "HPLC" means high pressure liquid chromatography, "m" means meter(s), "min" means minute(s), "mL" means milliliter(s), "mm" means millimeter(s), "MPa" means megapascal(s), "N" means normal, "psi" means pound(s) per square inch, "PTFE" means poly(tetrafluoroethylene), "rpm" means revolutions per minute, "wt %" means weight percent(age), "µL" means microliter(s), and "µm" means micrometer(s).

Materials

Amberlyst® A70 ion exchange resin was manufactured by Dow Chemical's Rohm and Haas division (Philadelphia, Pa.).

Xylose, sulfolane, and dimethylsulfoxide were obtained from Sigma-Aldrich Corporation (St. Louis, Mo.).

Zeolite CP7146 used in Example 3 was obtained from Zeolyst International (Conshohocken, Pa.)

The following solid acid catalysts were obtained from Zeolyst International, Conshohocken, Pa., or Conteka B. V. (now Zeolyst, International): Product #: CBV 400, CBV 500, CBV 712, CBV 720, CBV 760, CBV 780, CP 814C, CP 814E, CP 811B-200, CP 811C-300, CBV 3020, CBV 5020, CBV 1502, CBV 2802 (now CBV 28014), CBV 10A, CBV 20A, and CBV 30A. The solid acid catalyst S-115 (LA) was obtained from Union Carbide Corporation (now UOP, Des Plaines, Ill.). The solid acid catalyst Amberlyst™ 70 was obtained from Dow Chemical Company (Midland, Mich.). Amberlyst™ 70 is a macroreticular polymer based catalyst primarily comprising sulfonic-acid-functionalized styrene divinylbenzene copolymers. The solid acid catalyst 13% Nafion® on silica ($SiO_2$) was obtained from E. I. du Pont de Nemours and Co. (Wilmington, Del.). Nafion® is a registered trademark of E. I. du Pont de Nemours and Company for its perfluorinated sulfonic acid polymer products.

Deionized water was used unless otherwise indicated.

Analytical Methods

For Example 1 (Prophetic), Comparative Examples A and B

Furfural and sugar analysis is done by HPLC. Samples were collected and passed through a 0.2 μm syringe filter prior to analysis. The samples were neutralized with calcium carbonate and re-filtered before they were analyzed by high pressure liquid chromatography (HPLC). The HPLC instrument employed was a HP 1100 Series equipped with Agilent 1200 Series refractive index (RI) detector and an auto injector (Santa Clara, Calif.). The analytical method was adapted from an NREL procedure (NREL/TP-510-42623). Separation and quantitation of monomeric sugars (glucose, xylose, and arabinose), and furfural (FF) was performed by injecting the sample (10 μL) on to a Bio-Rad HPX-87P (Bio-Rad, Hercules, Calif.) column maintained at 85° C. Water was used as the eluant, with a flow-rate of 0.6 mL/min. The reaction products in the eluant were identified with the RI detector operating at 55° C.

For Examples 2, 3, 4 and Comparative Example C

Distillates and reaction flask contents were analyzed on a calibrated Aminex HPX-87H HPLC column (Bio-Rad Company) using a refractive index detector, and the column wash was analyzed via gas chromatographic analysis using a flame ionization detector and a calibrated 30 m HP-INNOWax GC column (Agilent Technologies).

Prophetic Example 1

Conversion Via Reactive Distillation of Sugar Solution to Furfural with Solid Acid Catalyst A solution of 10 wt % pentose and pentose oligomers with less than 1 wt % hexose and hexose oligomers is fed to a distillation column. The 1 inch (2.54 cm) diameter stainless steel distillation column has 5 trays located above the feed point and 5 trays with enhanced hold up time per tray loaded with Amberlyst™ A70 sulfonic acid ion exchange resin beads. The column is refluxing water upon startup at a temperature of 180° C. and pressure of 120 psi (0.827 MPa). Feed is begun at 5 grams per minute above the stripping/reactive section of the column, and the material reacts to produce a material comprising furfural, water and high boilers The reboiler of the distillation column is level controlled with a flow out of 1.33 grams per minute analyzing at, for example, 0.5 wt % in pentose and hexose and oligomers, 8.3 wt % in humins and other high boilers (present primarily as solids), and about 91.2 wt % water. Furfural is not detectable in the reboiler material. The distillate is removed at a rate of 3.67 grams per minute at the top of the column with a composition of, for example, 7.0 wt % furfural, the remainder comprising primarily water. The steady state yield to furfural from pentose and pentose oligomers of the process as run in this example would be 70.0%.

Example 1

Production of Furfural with Solid Acid Catalysts

Zeolites having different frameworks were used as catalysts as indicated in Table 1, including faujasite (FAU), zeolite beta (BEA), ZSM-5 (MFI), and mordenite (MOR). All zeolites were calcined at 550° C. for 8 h in air prior to use. All of the zeolites are in proton form after calcining except for CBV 10A which was in the sodium form. The polymer catalysts Amberlyst™ 70 and 13% Nafion on silica were used as obtained.

The following amounts and variables were the same for all experiments in this Example: 1) solvent was sulfolane, 2) mass of solvent was 5 g, 3) mass of solid catalyst was 0.075 g (1.5% of the solvent mass), 4) aqueous xylose solution concentration was 5 wt %, 5) xylose solution addition rate was 0.4 mL/min, 6) stirring rate was approximately 500 rpm, 7) reaction run time was 40 min, 8) average reaction temperature was 170° C., 9) oil bath temperature was 250° C., and 10) the internal standard added for analysis was dimethylsulfoxide.

The conversion of xylose to furfural was carried out in a 10 mL three-necked round bottomed flask (Chemglass, Inc. Life Sciences Catalog No. PN CG-1507-03) containing a PTFE-coated stirring bar (VWR Company Catalog No. 58949-010), a thermowell, a threaded adapter with cap (Chemglass, Inc. Life Sciences Catalog No. CG-350-01), and a PTFE-lined silicon septum (National Scientific Catalog No. B7995-15). The flask was connected to a vacuum-jacketed Vigreux distillation column (Chemglass, Inc. Life Sciences Catalog No. CG-1242) loaded with 8.0 g of 4 mm diameter glass beads (Chemglass, Inc. Life Sciences Catalog No. CG-1101-03). The beads were held in place at the bottom of the distillation column with a piece of 1/16" diameter thick fluoropolymer film that was approximately ¾" wide by 3" long which was either wound up into a coil or folded so that it contained pleats. A 20 mL plastic syringe with Luer lock tip (Chemglass, Inc. Life Sciences Catalog No. PN 309661) was connected to 1/16" fluoropolymer tubing which was pierced through the septum. Addition of the xylose solution from the syringe to the reaction vessel was controlled with a digital syringe pump. The reactions were carried out under an atmosphere of nitrogen.

To the reaction flask were added 5 g of solvent and 0.075 g of solid acid catalyst. The syringe on the syringe pump was filled with an aqueous xylose solution which was weighed prior to addition, and then reweighed after the completion of addition to determine the total amount of xylose solution added to the reaction mixture. After the flask was loaded, it was attached to the distillation column and one end of the 1/16" diameter fluoropolymer tube was attached to the syringe containing the aqueous xylose solution and the other end was inserted through the septum and into the reactor. The flask was lowered into the hot oil to bring the reactor contents to the desired internal temperature and addition of the xylose solution from the syringe using the syringe pump was started. The xylose solution was added at a constant rate and the temperature of the reaction mixture was maintained as constant as possible by slight adjustments to the height of the apparatus in the oil bath. At the end of the reaction, the syringe pump was stopped, the tube was pulled from the reaction flask and the apparatus was raised out of the oil bath.

The amount of distillate collected was weighed, a measured amount of the internal standard (dimethylsulfoxide) was added for analytical purposes, and the solution was then mixed until it was homogeneous (additional water was added to dilute the mixture if necessary). The reaction flask was removed from the distillation head and was weighed to determine the mass of material in the flask. A measured amount of internal standard (dimethylsulfoxide) was added to the reaction flask and it was mixed well. The contents of the reaction flask were then transferred to a 50 mL centrifuge tube. The distillation head was washed with water and the washes were also used to wash the reboiler. All the washes were combined in the 50 mL centrifuge tube, and solids were centrifuged to the bottom of the tube using the supernatant for analysis.

The distillate, reaction flask contents, and the washes were then analyzed by HPLC on a calibrated Biorad Aminex HPX-87H column using a refractive index detector. An aqueous 0.01 N $H_2SO_4$ isocratic mobile phase flowing at 0.6 mL/min through a column heated to 65° C. and a refractive index detector heated to 55° C. The detected amounts of xylose and furfural were recorded. Results for different solid acid catalysts are presented in Table 1.

TABLE 1

| Run | Original Catalyst Source | Catalyst Type or Zeolite Framework Type | Mole Ratio Si/Al in Catalyst | Mole Ratio (Al/Al + Si) in Catalyst | Surface Area (m²/g) | Xylose Conversion (%) | Selectivity to Furfural (%) | Yield of Furfural (%) |
|---|---|---|---|---|---|---|---|---|
| 1.1 | CP814E | BEA | 12.5 | 0.074 | 680 | 99 | 74 | 73 |
| 1.2 | CP814C | BEA | 19 | 0.05 | 710 | 97 | 74 | 72 |
| 1.3 | CP 811B-200 | BEA | 100 | 0.01 | — | 94 | 67 | 63 |
| 1.4 | Amberlyst ™ 70 | polymer | — | — | — | 93 | 63 | 59 |
| 1.5 | CP 811C-300 | BEA | 150 | 0.007 | 620 | 91 | 62 | 57 |
| 1.6 | CBV 720 | FAU | 15 | 0.063 | 780 | 89 | 57 | 51 |
| 1.7 | CBV 3020 | MFI | 15 | 0.063 | 405 | 92 | 55 | 51 |
| 1.8 | CBV 30A | MOR | 15 | 0.063 | 600 | 91 | 55 | 50 |
| 1.9 | CBV 780 | FAU | 40 | 0.024 | 780 | 90 | 55 | 49 |
| 1.10 | CBV 760 | FAU | 30 | 0.032 | 720 | 92 | 52 | 48 |
| 1.11 | CBV 20A | MOR | 10 | 0.091 | 500 | 91 | 53 | 48 |
| 1.12 | CBV 712 | FAU | 6 | 0.143 | 730 | 87 | 47 | 41 |
| 1.13 | CBV 1502 | MFI | 75 | 0.013 | 420 | 86 | 46 | 40 |
| 1.14 | 13% Nafion/$SiO_2$ | polymer | — | — | — | 91 | 44 | 40 |
| 1.15 | CBV 2802 | MFI | 140 | 0.007 | 411 | 88 | 43 | 38 |
| 1.16 | CBV 5020 | MFI | 25 | 0.038 | 425 | 87 | 42 | 37 |
| 1.17 | CBV 500 | FAU | 2.60 | 0.278 | 750 | 84 | 29 | 24 |
| 1.18 | CBV 400 | FAU | 2.55 | 0.282 | 730 | 83 | 25 | 20 |

The catalysts that gave the highest yields in these experiments were the beta zeolites, particularly catalysts derived from calcinations of CP814C and CP814E. Amberlyst™ 70 also gave high yields and conversion.

Example 2

Dehydration of Xylose to Furfural Via Reactive Distillation with Solid Acid Catalyst The reactive distillation unit used here consisted of a jacketed glass tube reactor. The glass reactor, present inside the outer jacket, had a length of 8.5 inch (21.6 cm) and an outer diameter of 1.38" (3.5 cm). The glass reactor was filled with about 10 gm of beta-zeolite catalyst (granules). The catalyst was provided by Zeolyst International (product # CP814E, lot #2200-42, $SiO_2$:$Al_2O_3$ mol ratio 25:1, Si:Al ratio 12.5:1, surface area 680 m²/g) in a powder form. The powder was calcined in air at 550° C. for about 8 h. The calcined powder was then charged in stainless steel die and pressed at $1.82 \times 10^5$ kPa using a Preco hydraulic press. The resulting slugs (25 mm diameter×~25 mm thick) were crushed and sieved to produce granules of −12/+14 mesh (1.40 mm-1.70 mm). These beta-zeolite granules were used as catalyst in this study.

The catalyst bed was positioned in the middle of the glass reactor and the rest of the reactor was packed with glass beads (Chemglass Inc. Catalog No. CG-1101-01) of 2 mm diameter, placed above (stripping section) and below the reactor. A stainless steel mesh was placed below the glass beads (in the bottom portion of the reactor) to support the catalyst bed and glass beads. A thermocouple was used to monitor the catalyst bed temperature and was placed inside a thermowell located in middle of the glass reactor.

The inner glass reactor was surrounded by an outer jacket (Outer diameter: 5.7 cm) through which an oil (Lauda Brinkmann LZB 222, THERM240) was circulated continuously in order to maintain the reactor temperature at a desired value. A high temperature oil bath (Neslab Exacal EX-250HT) was used to control the oil temperature, and the flow rate of the oil through the outer jacket of the reactor. The oil bath temperature was kept at 195-200° C. so that an average temperature of about 175° C. was maintained in the catalyst bed (placed inside the glass reactor).

A distillation head including a condenser was attached to the top of the reactor, where a temperature of 15° C. was maintained constant with a continuous circulation of a coolant mixture containing 50 wt. % ethylene glycol (VWR, BDH 2033) and 50 wt. % water. A circulation bath (Lauda Ecoline Staredition RE112) was used for this purpose.

The reactor was connected to a continuous flow system capable of precisely controlled liquid feed delivered by an HPLC Pump (Lab Alliance Series I). In this particular study of catalyst activity and stability for a beta-zeolite catalyst sample, a feed consisting of 5 wt. % xylose (Sigma Aldrich, X1500) in a mixture that contained 15 wt % water and 80 wt. % high boiling solvent, sulfolane (Sigma Aldrich, T22209), was loaded to the HPLC pump. The feed rate (to the reactor) was maintained constant at 0.75 ml/min. A glass container filled with the above feed solution was kept on a balance to continuously monitor the amount of feed introduced to the reactor. The feed was introduced above the catalyst bed at the specified feed rate. The stripping section (containing glass beads) also aided in uniformly distributing the liquid feed to the catalyst bed. The feed mixture reacted on the catalyst bed to form furfural, which was the desired product of this reaction along with some high boilers and water. Water and furfural being low boilers, formed vapors and traveled to the distillation head containing the condenser. The vapors were then condensed and were collected in a glass flask (250 ml, Chemglass Inc., Catalog No. CG-1559-10) surrounded by an ice bath (for the purpose of providing a low temperature atmosphere for further cooling the vapors). One of the necks of this flask was sealed with a rubber septum. A 10 ml plastic syringe with Luer lock tip (BD, REF 309604) was connected to a needle which was pierced through the septum. This syringe was used to collect the distillate sample at regular intervals. The reaction was carried out under atmospheric pressure.

The reactive distillation unit was also equipped with a reflux valve, which was closed (reflux ratio=0), in order to avoid the reaction between furfural (with itself, forming oligomers of furfural) and xylose further resulting in the formation of high boilers, commonly known as humins. The unreacted feed (containing xylose and sulfolane) along with high boilers (humins) formed during the reaction was collected in the reboiler located below the reactor. The reboiler was a 3-necked round-bottom glass flask (250 ml, Chemglass Inc., Catalog No. CG-1530-01). A 20 ml plastic syringe with Luer lock tip (BD 20 ml syringe REF 309661) was connected to a needle, which was pierced through a rubber septum used to seal one of the necks of the round bottom flask. This syringe was used to collect the reboiler sample at regular intervals. Another neck of the round bottom flask was sealed with a rubber septum and a 1/8" Teflon tubing (Chemglass Inc., Catalog No. CG-1037-10) was pierced through the septum into the reboiler. This tubing was used to introduce water to the reboiler at a constant rate of 0.50 ml/min maintained with the help of a digital syringe pump (KD Scientific, Model No. KDS KEGATO 270, Catalog No. 78-8270). The reboiler was kept heated at a temperature of 160° C. With this sufficient high temperature and a continuous input of water in the reboiler, there was a steady formation of steam which traveled up through the catalyst bed and further helped to effectively remove furfural (by forming an azeotrope) from the reaction zone. Thus the steam stripping brings additional advantage of effective furfural separation from the reaction zone. $N_2$ was also introduced in one of the necks of the reboiler, for further removal of furfural from the reaction zone.

The samples (both distillate and reboiler) were collected in glass vials and weighed. The reboiler samples collected during the reactive distillation run were analyzed by HPLC on a calibrated Biorad Aminex HPX-87H column using a refractive index detector. An aqueous 0.01 N H2SO4 isocratic mobile phase flowing at 0.6 ml/min through a column heated to 65° C. and a refractive index detector heated to 55° C. A measured amount of the internal standard (dimethylsulfoxide) was added for analytical purposes, and the solution was then mixed until it was homogeneous. The detected amounts of xylose and furfural were recorded. The distillate samples were analyzed by an Agilent 6890GC equipped with a 30 meter DB-1 capillary column (J&W 125-1032). 5 microliters of solution was injected into an injector port set to 175° C. with a split ratio of 5:1, a total helium flow of 55.2 ml/min, a split flow of 44.4 ml/min and a head pressure of 6.25 psi. The oven temperature was held at 50° C. for 2 min and then it was increased to 110° C. at 10° C./min followed by a second increase to 240° C. at 20° C./min. A flame ionization detector set at 250° C. was used to detect signal. A measured amount of the internal standard (1-pentanol) was added for the GC analysis. The detected amounts of furfural were recorded. Results obtained during the dehydration of xylose to furfural using beta-zeolite catalyst have been presented in Table 2.

Table 2 below shows the result of a 3-day run (140 min on day 1, 390 min on day 2 and 150 min on day 3) carried out for about 12 hours (under identical conditions of temperature, flow rate, etc.). The data are reported for the steady state conditions achieved in the reactor. As seen in the table 2, the beta-zeolite catalyst resulted in xylose conversion of greater than 95%. The furfural yields (and hence the selectivity towards furfural) were nearly steady over the entire run.

TABLE 2

Dehydration of Xylose to Furfural via Reactive Distillation Using beta-Zeolite Catalyst and a Feed Containing 5 wt. % Xylose, 15 wt. % Water and 80 wt. % Sulfolane.

| Time (min) | Xylose Conversion | Furfural Yield | Furfural Selectivity |
|---|---|---|---|
| 80 | 99.5% | 66.8% | 67.2% |
| 110 | 99.3% | 72.7% | 73.2% |
| 140 | 98.9% | 69.2% | 70.0% |
| 290 | 96.9% | 69.4% | 71.7% |
| 350 | 95.5% | 69.7% | 73.0% |
| 410 | 94.5% | 69.5% | 73.6% |
| 470 | 96.4% | 65.0% | 67.5% |
| 680 | 97.8% | 70.3% | 71.8% |

Example 3

Xylose Reactive Distillation Using H-Mordenite Catalyst

Above experimental set up (in Example 3) was then used to study the dehydration of xylose to furfural reaction using H-mordenite catalyst. The H-mordenite catalyst used here was provided by Zeolyst International (Product # CBV21A, lot #2200-77, $SiO_2/Al_2O_3$ mol ratio 20:1, Si:Al ratio 10:1, surface area 500 $m^2$/g) in a powder form. The powder catalyst was then calcined and converted into granules using a similar technique described earlier for the beta-zeolite catalyst. The rest of the experimental conditions were the same as used earlier for the beta-zeolite catalyst (feed composition: 5 wt. % xylose, 15 wt. % water, 80 wt. % sulfolane; feed flow rate=0.75 ml/min; water flow rate in the pot=0.50 ml/min; pot temperature=160° C., etc.) The reactor temperature was maintained in the range of 175-180° C. Table 3 summarizes the results for the H-mordenite catalyst.

TABLE 3

Dehydration of Xylose to Furfural via Reactive Distillation Using H-mordenite Catalyst and a Feed Containing 5 wt. % Xylose, 15 wt. % Water and 80 wt. % Sulfolane.

| Time (min) | Xylose Conversion | Furfural Yield | Furfural Selectivity |
|---|---|---|---|
| 70  | 99.0% | 63.4% | 64.0% |
| 105 | 98.8% | 72.7% | 73.6% |
| 165 | 97.7% | 74.5% | 76.3% |
| 225 | 97.0% | 74.6% | 76.9% |
| 290 | 98.5% | 82.4% | 83.6% |

Example 3 gives an example of production of furfural with reactive distillation utilizing a high boiling solvent resulting in a higher yield than seen in the Comparative Examples. Example 4 shows an even higher yield of furfural than seen in Example 3.

Comparative Example A described below gives a comparison run using a fixed bed reactor with an acidic ion exchange resin and no high boiling solvent with a much poorer resulting yield and selectivity to furfural. Comparative Example B described below gives a comparison with a fixed bed reactor using a beta Zeolite catalyst and a high boiling solvent, similar to that used in example 3, with a worse result for yield.

Comparative Example A

Lab-Scale Continuous Process: Fixed Bed Reactor with Aqueous Xylose Feed and Strongly Acidic Ion Exchange Resin Catalyst A 5 inch (12.7 cm) long, ½" (1.27 cm) outer diameter of 316 stainless steel tubing (Swagelock Corporation) was used as a fixed bed reactor. The catalyst bed was supported by a ⅜" (0.952 cm) steel tube at the bottom of the upflow arrangement, with a stainless mesh supported by this tube as bed support for the catalyst. The reactor tube was loaded with 3 cm³ of Amberlyst™ A70 ion exchange resin. The reactor was then connected to a continuous flow system capable of precisely controlled liquid feed delivered by an ISCO D-500 Syringe Pump (Teledyne ISCO, Lincoln Nebr., USA). The reactor was installed within a tube furnace which allowed temperature control of the catalyst bed as read by an internal 1/16" (15.9 mm) stainless steel thermocouple. The flow exiting the reactor was then pressure controlled by a Swagelock backpressure regulator capable of up to 1000 psig (6.89 MPa-g) at the chosen liquid flows. The product from the regulator was then collected in sample vials for analysis by HPLC.

In the study of catalyst activity and lifetime for Amberlyst™ A70, the feed was 4 wt % xylose in water, loaded to the ISCO pump. The solution was fed through the reactor which was loaded as described previously with 3 cm³ of Amberlyst™ A70 acidic ion exchange resin. The reactor was controlled at 160° C. via a tube furnace and the pressure was controlled at 200 psig (1.38 MPa-g) by a backpressure regulator. Table 4 below shows the result of a continuous run where the flowrate was changed to study the effect of space velocity on the xylose conversion and furfural yield in an upflow fixed bed system. Also shown in the table is a calculated first order rate constant (k) for xylose conversion which permits comparison of catalyst activity as a function of time. As seen in the table, the activity is low from the start of the run, with a dramatic decrease over the course of the experiment. The buildup of humins is believed to be the primary cause of catalyst activity loss.

TABLE 4

Furfural Production in a Fixed Bed Solid Acid Reactor with Time

| Time on Stream (h) | Space velocity 1/h | Xylose Conversion | Furfural Yield | Furfural Selectivity | k (1/min) | % Initial Activity |
|---|---|---|---|---|---|---|
| 2.5  | 16 | 40.4% | 11.6% | 28.9% | 0.138 | 100.0% |
| 2.7  | 16 | 40.6% | 11.3% | 27.8% | 0.139 | 100.6% |
| 3.8  | 32 | 20.2% | 7.5%  | 37.2% | 0.120 | 87.2%  |
| 3.9  | 32 | 23.1% | 7.1%  | 30.9% | 0.140 | 101.6% |
| 22.5 | 4  | 30.4% | 8.8%  | 29.0% | 0.024 | 17.6%  |
| 23.0 | 4  | 31.5% | 8.5%  | 27.1% | 0.025 | 18.3%  |
| 27.1 | 8  | 14.7% | 4.8%  | 32.5% | 0.021 | 15.4%  |
| 27.3 | 8  | 11.6% | 5.0%  | 43.0% | 0.016 | 11.9%  |
| 29.3 | 16 | 9.4%  | 2.8%  | 29.7% | 0.026 | 19.2%  |
| 29.5 | 16 | 9.6%  | 2.7%  | 27.8% | 0.027 | 19.5%  |
| 35.2 | 2  | 46.6% | 12.4% | 26.6% | 0.021 | 15.2%  |
| 35.4 | 2  | 46.4% | 12.1% | 26.0% | 0.021 | 15.1%  |

Comparative Example B

Lab-Scale Continuous Process: Fixed Bed Reactor with Sulfolane Solvent. and Zeolite Beta Catalyst The apparatus of Example 2 was used with a high boiling water-miscible solvent. Sulfolane, in addition to being high boiling, is an excellent solvent for biomass and humins (by-products from furfural synthesis). It is hoped that use of such a solvent will increase the lifetime of a solid acid catalyst used for production of furfural from xylose.

In the study of catalyst activity and lifetime for a Zeolite Beta sample, the feed was 4 wt % xylose in a mixture that contained 10 wt % water and 86 wt % sulfolane, loaded to the ISCO pump. CP 7146 (Zeolyst International) is an extruded form of ammonium-beta (CP 814E (Zeolyst), Si/Al=12.5). The sample was calcined by heating in air to 525 deg C. at a rate of 10 deg C./min, then 2 deg C./min to 540 deg C. and finally 1 deg C./min to 550 deg C. where the sample was held for 8 hours. 1.4935 grams of CP 7146 was loaded to the tubular reactor of Comparative Example A. The reactor was controlled at 160° C. via a tube furnace and the pressure was controlled at 200 psig (1.38 MPa-g) by a backpressure regulator. Table 5 below shows the result of a continuous run where the flowrate was changed to study the effect of space velocity on the xylose conversion and furfural yield in an upflow fixed bed system. Also shown in the table is a calculated first order rate constant (k) for xylose conversion which permits comparison of catalyst activity as a function of time. As seen in the table, the activity is much better in sulfolane solvent than in an aqueous system such as Comparative Example A. There is however a dramatic decrease over the course of the experiment as seen in Comparative Example A. The buildup of humins is believed to be the primary cause of catalyst activity loss. The use of sulfolane solvent, which solubilizes humins, apparently does not prevent the deactivation of the catalyst.

TABLE 5

Furfural Production in a Fixed Bed Solid Acid Reactor with Time, Sulfolane Solvent with Zeolite Beta Catalyst

| Time on Stream (h) | Space velocity 1/h | Xylose Conversion | Furfural Yield | Furfural Selectivity | k (1/min) | % Initial Activity |
|---|---|---|---|---|---|---|
| 4.0  | 8 | 94.5% | 44.0% | 46.5% | 0.386 | 100.0% |
| 4.2  | 8 | 94.5% | 43.9% | 46.5% | 0.386 | 100.1% |
| 21.0 | 2 | 99.5% | 50.5% | 50.7% | 0.174 | 45.1%  |

TABLE 5-continued

Furfural Production in a Fixed Bed Solid Acid Reactor with
Time, Sulfolane Solvent with Zeolite Beta Catalyst

| Time on Stream (h) | Space velocity 1/h | Xylose Conversion | Furfural Yield | Furfural Selectivity | k (1/min) | % Initial Activity |
|---|---|---|---|---|---|---|
| 21.3 | 2 | 99.5% | 50.5% | 50.8% | 0.174 | 45.1% |
| 25.7 | 8 | 66.3% | 30.5% | 46.0% | 0.145 | 37.6% |
| 25.9 | 8 | 64.9% | 30.1% | 46.3% | 0.140 | 36.2% |
| 29.4 | 8 | 91.4% | 46.7% | 51.1% | 0.328 | 85.0% |
| 29.8 | 8 | 91.0% | 46.3% | 50.9% | 0.321 | 83.3% |
| 33.8 | 8 | 42.4% | 8.4% | 19.8% | 0.074 | 19.1% |
| 34.0 | 8 | 42.2% | 8.4% | 19.8% | 0.073 | 19.0% |
| 36.4 | 16 | 31.7% | 2.5% | 7.8% | 0.102 | 26.3% |
| 36.6 | 16 | 32.0% | 2.6% | 8.2% | 0.103 | 26.7% |
| 50.9 | 2 | 71.6% | 22.1% | 30.9% | 0.042 | 10.9% |
| 51.5 | 2 | 71.9% | 22.3% | 31.0% | 0.042 | 11.0% |

Comparative Example C

Using an analogous procedure as described in Example 2, the materials derived from S-115 (LA) and CBV 10A after calcination were tested as catalysts for production of furfural. The results are presented in Table 6.

TABLE 5

| Run | Catalyst Name | Catalyst Type | Mole ratio Si/Al in Catalyst | Mole ratio (Al/Al + Si) in Catalyst | Surface Area (m²/g) | Xylose Conversion (%) | Selectivity to Furfural (%) | Yield of Furfural (%) |
|---|---|---|---|---|---|---|---|---|
| C.a | S-115 (LA) | MFI | 400 | 0.002 | 411 | 77 | 1 | 0 |
| C.b | CBV 10A | MOR | 5 | 0.167 | 425 | 15 | 0 | 0 |

The catalysts derived from S-115 (LA), a zeolite with very low aluminum content, and CBV 10A, a zeolite with sodium cations and few Bronsted acid sites, showed 0% yield of furfural in Run A and Run B. This demonstrated that zeolites with a low number of Brönsted acid sites, or low aluminum content (very high Si/Al ratio, greater than or equal to 400) were not good catalysts for furfural production from $C_5$ and/or $C_6$ sugars.

What is claimed is:

1. A process comprising:
   (a) providing a reactive distillation column comprising a top, a bottom, a reaction zone in between the top and the bottom, and a solid acid catalyst disposed in the reaction zone;
   (b) contacting a feedstock solution with the solid acid catalyst in the presence of sulfolane in the reaction zone for a residence time sufficient to produce a mixture of water and furfural, wherein the sulfolane forms a monophasic solution with water in the reaction zone at a temperature in the range of 90-250° C. and a pressure in the range of 0.1-3.87 MPa, wherein the feedstock solution comprises $C_5$ sugar, $C_6$ sugar or a mixture thereof;
   (c) removing the mixture of water and furfural from the top of the reactive distillation column; and
   (d) collecting water, unreacted sugars, and nonvolatile byproducts dissolved in the sulfolane from the bottom of the reactive distillation column in a reboiler.

2. The process according to claim 1, wherein the acid catalyst comprises a heterogeneous heteropolyacid, a salt of a heterogeneous heteropolyacid, a natural or synthetic clay mineral, a cation exchange resin, a metal oxide, a mixed metal oxide, a metal sulfide, a metal sulfate, a metal sulfonate, sulfated titania, sulfated zirconia, a metal nitrate, a metal phosphate, a metal phosphonate, a metal molybdate, a metal tungstate, a metal borate, or a combination of any of these.

3. The process according to claim 2, wherein the acid catalyst comprises a clay mineral that is a zeolite.

4. The process according to claim 3, wherein the acid catalyst is a medium or large pore, acidic, hydrophobic zeolite.

5. The process according to claim 4, wherein the zeolite comprises ZSM-5, faujasite, beta zeolite, Y zeolite, mordenite, or a combination of any of these.

6. The process according to claim 1 further comprising:
   e. removing water and unreacted sugars from the water, unreacted sugars and nonvolatile byproducts of step (d); and
   f. concentrating by evaporation at least a portion of the water and unreacted sugars and using it as feedstock solution in step (b).

7. The process according to claim 1 further comprising separating the furfural from the removed water and furfural of step (c).

8. The process according to claim 1 wherein the combined concentration of $C_5$ sugar and/or $C_6$ sugar in the feedstock solution is in the range of 1-99 weight percent based on the total weight of the feedstock solution.

9. The process according to claim 8 wherein the combined concentration of $C_5$ sugar and/or $C_6$ sugar in the feedstock solution is in the range of 5-35 weight percent based on the total weight of the feedstock solution.

10. The process according to claim 1 wherein the feedstock solution comprises xylose, glucose, or a mixture thereof.

11. The process according to claim 1, wherein the feedstock further comprises sulfolane.

12. The process according to claim 1, further comprising a steam-stripping step, comprising feeding water or steam to the reaction zone from the bottom of the reactive distillation column.

13. The process of claim 1 further comprising the steps of:
   h) diluting at least a portion of the contents of the reboiler with water or with the feedstock solution, thereby precipitating water-insoluble byproducts;
   i) removing the byproducts precipitated in step h); and
   j) feeding the precipitate-free solution remaining after step i) back to the reaction zone.

14. A process comprising the steps of:
   (a) providing a reactor comprising a reactive distillation column comprising an upper, rectifying section; a lower, stripping section; and a reboiler, wherein the stripping section is a reaction zone containing a solid acid catalyst,
   (b) continuously feeding a feedstock solution comprising $C_5$ sugar, $C_6$ sugar or a mixture thereof to the column at a location between the rectifying section and the stripping section, allowing the solution to flow into the reaction zone into contact with the solid acid catalyst in the presence of sulfolane, thereby forming a reaction mixture, wherein (i) the sulfolane forms a monophasic solution with water in the reaction zone at a temperature of the reaction mixture between about 90° C. and about 250° C. and at a pressure between atmospheric pressure and 3.87 MPa, and (iii) the sugar solution and catalyst are in contact for a time sufficient to produce water and furfural (c) drawing off a mixture of furfural and water at the top of the column;

(d) collecting water, unreacted sugars, and nonvolatile byproducts dissolved in the sulfolane in the reboiler;

(e) removing nonvolatile byproducts from the reboiler; and (f) removing the water and unreacted sugars from the reboiler for further use or disposal.

* * * * *